US011308608B2

(12) United States Patent
Jeon et al.

(10) Patent No.: US 11,308,608 B2
(45) Date of Patent: Apr. 19, 2022

(54) APPARATUS AND METHOD FOR MEDICAL DIAGNOSTIC

(71) Applicants: SAMSUNG SDS CO., LTD., Seoul (KR); SAMSUNG LIFE PUBLIC WELFARE FOUNDATION, Seoul (KR)

(72) Inventors: Eun-Joo Jeon, Seoul (KR); Sung-hoon Joo, Seoul (KR); Soon-Hwan Kwon, Seoul (KR); Myung-Jin Chung, Seoul (KR)

(73) Assignees: SAMSUNG SDS CO., LTD., Seoul (KR); SAMSUNG LIFE PUBLIC WELFARE FOUNDATION, Seoul (KR)

(*) Notice: Subject to any disclaimer, the term of this patent is extended or adjusted under 35 U.S.C. 154(b) by 97 days.

(21) Appl. No.: 16/664,832

(22) Filed: Oct. 26, 2019

(65) Prior Publication Data
US 2021/0090247 A1 Mar. 25, 2021

(30) Foreign Application Priority Data
Sep. 23, 2019 (KR) .................. 10-2019-0116913

(51) Int. Cl.
*G06K 9/00* (2022.01)
*G06T 7/00* (2017.01)
(Continued)

(52) U.S. Cl.
CPC .......... *G06T 7/0012* (2013.01); *G06K 9/6256* (2013.01); *G06K 9/6267* (2013.01);
(Continued)

(58) Field of Classification Search
CPC ..................................................... G06T 15/08
See application file for complete search history.

(56) References Cited

U.S. PATENT DOCUMENTS

2018/0315193 A1* 11/2018 Paschalakis ............. G06N 3/08
2019/0197347 A1* 6/2019 Okuda .................... G06T 15/08
(Continued)

FOREIGN PATENT DOCUMENTS

KR   10-1881223 B1   7/2018

OTHER PUBLICATIONS

Chen, Xiaoran, and Ender Konukoglu. "Unsupervised detection of lesions in brain mri using constrained adversarial auto-encoders." arXiv preprint arXiv:1806.04972 (2018). (Year: 2018).*

*Primary Examiner* — Hadi Akhavannik
(74) *Attorney, Agent, or Firm* — The PL Law Group, PLLC

(57) ABSTRACT

A medical diagnostic method according to an embodiment includes receiving a plurality of slide images of a three-dimensional (3D) medical image obtained by capturing an object and clinical data for the object, extracting one or more slide images including a lesion among the plurality of slide images, extracting a region of interest (ROI) including the lesion from each of the extracted one or more slide images, generating latent space data including a feature of an image of the extracted ROI using a pre-trained deep learning-based ROI abstraction model, and generating a diagnostic result for the object from the latent space data and the clinical data using a pre-trained deep learning-based medical diagnostic model.

18 Claims, 10 Drawing Sheets

(51) Int. Cl.
*G16H 50/20* (2018.01)
*G16H 30/40* (2018.01)
*G06N 3/04* (2006.01)
*G06N 3/08* (2006.01)
*G06K 9/62* (2022.01)

(52) U.S. Cl.
CPC ........... *G06N 3/0454* (2013.01); *G06N 3/088* (2013.01); *G16H 30/40* (2018.01); *G16H 50/20* (2018.01); *G06T 2200/04* (2013.01); *G06T 2207/20081* (2013.01); *G06T 2207/20084* (2013.01); *G06T 2207/20212* (2013.01); *G06T 2207/30096* (2013.01); *G06V 2201/03* (2022.01)

(56) References Cited

U.S. PATENT DOCUMENTS

2019/0318476 A1* 10/2019 Isgum .................. A61B 6/5217
2020/0020098 A1*  1/2020 Odry ................... G06K 9/6245

* cited by examiner

FIG. 6
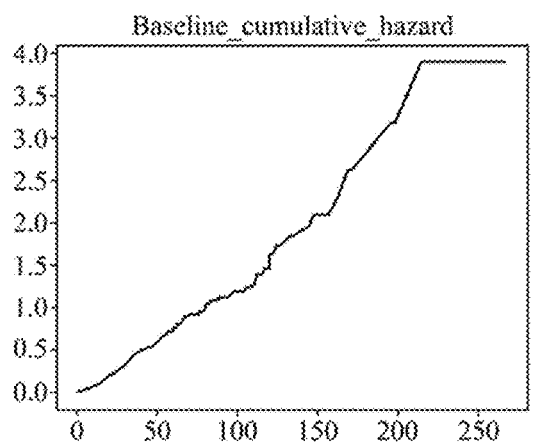
(a)
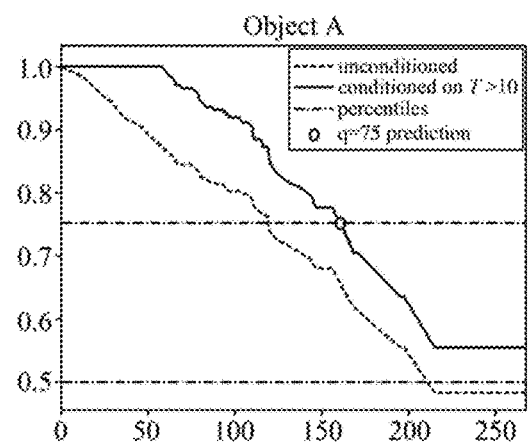
(b)
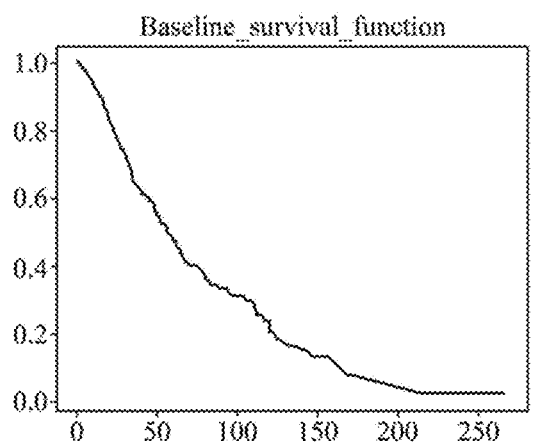
(c)
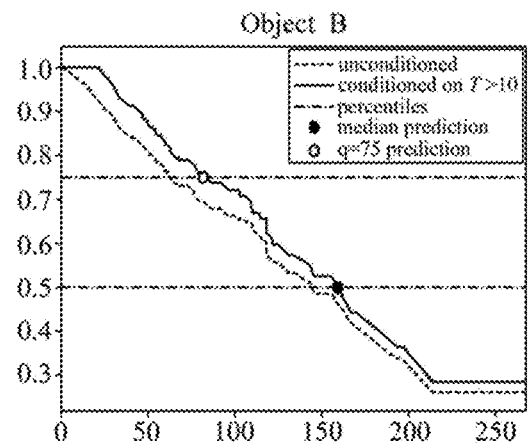
(d)

APPARATUS AND METHOD FOR MEDICAL DIAGNOSTIC

CROSS REFERENCE TO RELATED APPLICATIONS AND CLAIM OF PRIORITY

This application claims the benefit of Korean Patent Application No. 10-2019-0116913 filed on Sep. 23, 2019 in the Korean Intellectual Property Office, the disclosure of which is incorporated herein by reference in its entirety

TECHNICAL FIELD

Embodiments of the present disclosure relate to a medical diagnostic technique.

BACKGROUND ART

A medical image is an important factor for diagnosing a patient's disease or determining a treatment method. For example, breast cancer patients can be examined for breast cancer size, type, lymph node metastasis, and the like through Magnetic Resonance Imaging (MRI), Computed Tomography (CT), etc. Thus, cancer staging is determined, and patients will receive treatment appropriate for their cancer type. Medical images are first read visually by a specialist, and then are secondly read using quantitative results analyzed with statistical techniques.

Such a medical image analysis is a labor-intensive task that requires medical experts' time and effort. Accordingly, it is expensive for medical experts to analyze medical images, and it is not possible for the medical experts to handle all medical images, which are exponentially increasing due to the development of imaging technology. Thus, there are various attempts to reduce the burden on radiologist and to prevent human errors.

Conventionally, statistical techniques have been mainly used for medical image analysis. For example, information (e.g., mean, variance, skewness, kurtosis, or the like) related to the distribution of brightness and saturation of a medical image was extracted through histogram analysis or the like. Alternatively, a first derivative, a second derivative, or the like was extracted and the relationship (e.g., entropy, contrast, homogeneity, etc.) between pixels in the medical image was extracted through pollen analysis. The extracted information from medical image was used to diagnosis. However, since features extracted through statistical techniques are a hand-crafted feature, a systematic error may occur. Also, any loss of information may occur while image information is being reduced through statistical method, and thus the accuracy of the medical image analysis may be reduced.

Also, according to the conventional methods, only medical images that are unstructured data have been utilized for medical image analysis. A radiologist considers clinical information (e.g., height, age, disease, medication history, etc.) as well as medical images during image analysis. Accordingly, since medical images change depending on patients' conditions, it is difficult to trust the result of the diagnosis with only medical images. Also, the dimension of a medical image is much higher than the dimension of clinical information. Accordingly, when the dimensions of the medical image and the clinical information are not matched to each other, data having the medical image and the clinical image integrated therein cannot be used to train a medical image analysis model, and also the accuracy of the image analysis with deep learning model is reduced.

SUMMARY

Embodiments of the present disclosure are directed to providing a medical diagnostic method and apparatus.

According to an aspect of the present disclosure, there is a medical diagnostic method including receiving a plurality of slide images of a three-dimensional (3D) medical image obtained by capturing an object and clinical data for the object, extracting one or more slide images including a lesion among the plurality of slide images, extracting a region of interest (ROI) including the lesion from each of the extracted one or more slide images, generating latent space data including a feature of an image of the extracted ROI using a pre-trained deep learning-based ROI abstraction model, and generating a diagnostic result for the object from the latent space data and the clinical data using a pre-trained deep learning-based medical diagnostic model.

The extracting of one or more slide images may include extracting the one or more slide images using a convolutional neural network (CNN)-based lesion classification model that is pre-trained using a plurality of pre-collected slide images and a lesion classification result for each of the plurality of pre-collected slide images as training data.

The extracting of an ROI may include extracting the ROI using a CNN-based ROI extraction model that is pre-trained using a plurality of pre-collected slide images including a lesion and an ROI extraction result for each of the plurality of pre-collected slide images as training data.

The ROI abstraction model may include an encoder that is trained using images of a plurality of ROIs including a lesion as training data through variational auto-encoder (VAE).

The generating of latent space data may include generating the latent space data by using the encoder to encode the image of the extracted ROI.

The medical diagnostic model may be trained using a plurality of pieces of clinical data, a diagnostic result for each of the plurality of pieces of clinical data, and output data of the encoder that has received images of a plurality of ROIs including a lesion as training data.

The ROI abstraction model and the medical diagnostic model may be trained such that a sum of a resulting value of a loss function of each of the ROI abstraction model and the medical diagnostic model is minimized.

The sum of the resulting value of the loss function of each of the ROI abstraction model and the medical diagnostic model may be calculated through Equation 1 below:

$$L_{total} = \alpha \cdot \text{VAE\_loss} + \text{Diagnostic\_loss} \text{ (here, } 0 < \alpha) \quad \text{[Equation 1]}$$

where $L_{total}$ indicates the sum of the resulting value of the loss function of each of the ROI abstraction model and the medical diagnostic model, VAE_loss indicates a resulting value of a loss function of the ROI abstraction model, and Diagnostic_loss indicates a resulting value of a loss function of the medical diagnostic model.

The diagnostic result may include one of a survival rate, a treatment status, and a lesion type classification result.

The medical diagnostic method may further include, after the extracting of an ROI, generating a 3D ROI image obtained by combining the image of the extracted ROI of each of the extracted one or more slide images.

According to another aspect of the present disclosure, there is a medical diagnostic apparatus including a memory configured to store one or more instructions and one or more processors configured to execute the one or more instructions, wherein the one or more processors may receive a plurality of slide images of a three-dimensional (3D) medical image obtained by capturing an object and clinical data for the object, extract one or more slide images including a lesion among the plurality of slide images, extract a region of interest (ROI) including the lesion from each of the extracted one or more slide images, generate latent space data in which a feature of an image of the extracted ROI is included using a pre-trained deep learning-based ROI abstraction model, and generate a diagnostic result for the object from the latent space data and the clinical data using a pre-trained deep learning-based medical diagnostic model.

The one or more processors may extract the one or more slide images using a convolutional neural network (CNN)-based lesion classification model that is pre-trained using a plurality of pre-collected slide images and a lesion classification result for each of the plurality of pre-collected slide images as training data.

The one or more processors may extract the ROI using a CNN-based ROI extraction model that is pre-trained using a plurality of pre-collected slide images including a lesion and an ROI extraction result for each of the plurality of pre-collected slide images as training data.

The ROI abstraction model may include an encoder that is trained using images of a plurality of ROIs including a lesion as training data through variational auto-encoder (VAE).

The one or more processors may generate the latent space data by using the encoder to encode the image of the extracted ROI.

The medical diagnostic model may be trained using a plurality of pieces of clinical data, a diagnostic result for each of the plurality of pieces of clinical data, and output data of the encoder that has received images of a plurality of ROIs including a lesion as training data.

The ROI abstraction model and the medical diagnostic model may be trained such that a sum of a resulting value of a loss function of each of the ROI abstraction model and the medical diagnostic model is minimized.

The sum of the resulting value of the loss function of each of the ROI abstraction model and the medical diagnostic model may be calculated through Equation 1 below:

$$L_{total} = \alpha \cdot \text{VAE\_loss} + \text{Diagnostic\_loss} \text{ (here, } 0 < \alpha) \quad \text{[Equation 1]}$$

where $L_{total}$ indicates the sum of the resulting value of the loss function of each of the ROI abstraction model and the medical diagnostic model, VAE_loss indicates a resulting value of a loss function of the ROI abstraction model, and Diagnostic_loss indicates a resulting value of a loss function of the medical diagnostic model.

The diagnostic result may include one of a survival rate, a treatment status, and a lesion type classification result.

The one or more processors may generate a 3D ROI image obtained by combining the image of the extracted ROI of each of the extracted one or more slide images.

According to the disclosed embodiments, by using a deep learning algorithm to generate a diagnostic result for an object, a bias caused by variables generated due to the manual operation for medical image analysis may be reduced, and thus it is possible to increase the accuracy of the diagnostic result and to reduce the time required for medical image analysis due to the automation of the medical image analysis.

Also, according to the disclosed embodiments, by utilizing both of a medical image and clinical data to generate a diagnostic result, it is possible to sufficiently provide data usable by a deep learning-based medical diagnostic model, and it is also possible to prevent overfitting of the medical diagnostic model to increase the robustness of the medical diagnosis model. Also, it is possible to suggest a customized treatment that reflects a patient's characteristics.

BRIEF DESCRIPTION OF THE DRAWINGS

FIG. 6 is an exemplary diagram of a diagnostic result according to an embodiment;

DETAILED DESCRIPTION

Figure 1:
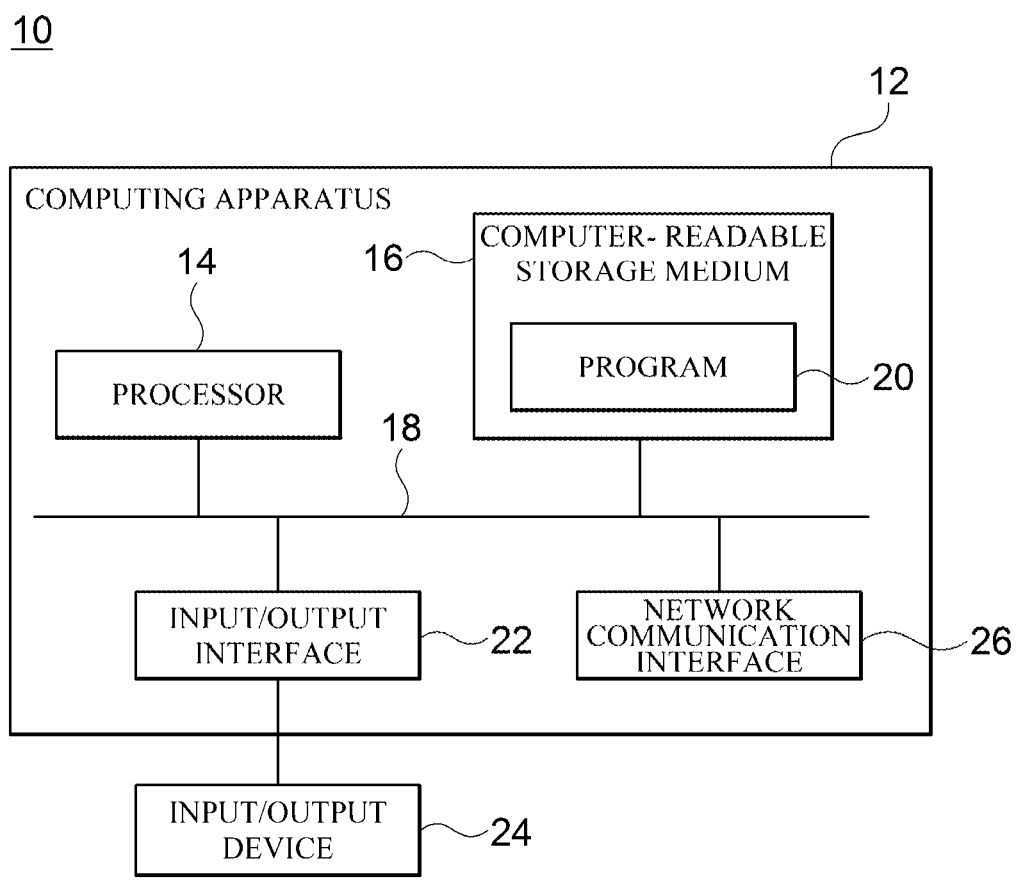
FIG. 1 is a block diagram illustrating a computing environment including a computing apparatus suitable for use in example embodiments.

Hereinafter, exemplary embodiments will be described with reference to the accompanying drawings. The following detailed description is provided to assist the reader in gaining a comprehensive understanding of methods, apparatuses, and/or systems described herein. However, this is merely an example, and the present invention is not limited thereto.

In describing the embodiments, when it is determined that a detailed description of a relevant known technique would unnecessarily obscure the subject matter of the present invention, the detailed description will be omitted. Also, terms used herein are defined in consideration of functions and may be changed depending on a user, the intent of an operator, or a custom. Therefore, the definition should be made based on the contents throughout the specification. The terminology used herein is only for the purpose of describing embodiments and are not limiting. The singular forms "a," "an," and "the" are intended to include the plural forms as well, unless the context clearly indicates otherwise. Also, it should be understood that the terms "comprises," "comprising," "includes," "includes,": and/or "including" specify the presence of stated features, integers, steps, operations, elements, components, and/or groups thereof when used herein, but do not preclude the presence or addition of one or more other features, integers, steps, operations, elements, components, and/or groups thereof.

Hereinafter, a neural network uses artificial neurons with simplified functions of biological neurons, and the artificial neurons may be connected to one another through a connection line having a connection weight. The connection weight, which is a parameter of the neural network, is a specific value of the connection line and may be referred to as a connection strength. The neural network may perform a human cognitive process or training process through artificial neurons. An artificial neuron may also be referred to as a node.

The neural network may include a plurality of layers. For example, the neural network may include an input layer, a hidden layer, and an output layer. The input layer may receive an input for performing training and deliver the input to the hidden layer. The output layer may generate an output of the neural network based on signals received from nodes in the hidden layer. The hidden layer may be located between the input layer and the output layer to change training data transferred through the input layer into a predictable value. Nodes included in the input layer and the hidden layer may be connected to each other through a connection line having a connection weight, and nodes included in the hidden layer and the output layer may be connected to each other through a connection line having a connection weight. Each of the input layer, the hidden layer, and the output layer may include a plurality of nodes.

The neural network may include a plurality of hidden layers. The neural network including the plurality of hidden layers is called a deep neural network, and training a deep neural network is called deep learning. A node included in the hidden layer is called a hidden node. In the following description, it may be understood that training a neural network indicates to train parameters of a neural network. Also, the trained neural network may be understood as a neural network to which the trained parameters are applied.

In this case, the neural network may be trained using a preset loss function as an indicator. The loss function may be an indicator to determine an optimal weight parameter for the neural network through training. The neural network may be trained with the goal of minimizing the resulting value of the preset loss function.

The neural network may be trained through supervised learning or unsupervised learning. The supervised learning is a method of inputting training data and output data corresponding to the training data to a neural network and updating connection weights of connection lines so that the output data corresponding to the training data is output. The unsupervised learning is a method of inputting only training data to a neural network without output data corresponding to the training data and updating connection weights of connection lines so that the feature or structure of the training data is ascertained.

FIG. 1 is a block diagram illustrating a computing environment 10 including a computing apparatus suitable for use in example embodiments. In the illustrated embodiment, each component may have a function and capability that differ from those described below, and an additional component may be included in addition to those in the following description.

As shown, the computing environment 10 includes a computing apparatus 12. In an embodiment, the computing apparatus 12 may be a medical diagnostic apparatus according to disclosed embodiments. The computing apparatus 12 includes at least one processor 14, a computer-readable storage medium 16, and a communication bus 18. The processor 14 may enable the computing apparatus 12 to operate according to the aforementioned example embodiment. For example, the processor 14 may execute one or more programs stored in the computer-readable storage medium 16. The one or more programs may include one or more computer-executable instructions which may be configured to enable the computing apparatus 12 to perform operations according to an example embodiment when the operations are executed by the processor 14.

The computer-readable storage medium 16 is configured to store computer-executable instructions, program codes, program data, and/or other suitable forms of information. The program 20 stored in the computer-readable storage medium 16 includes a set of instructions executable by the processor 14. In an embodiment, the computer-readable storage medium 16 may be a memory (a volatile memory such as a random access memory, a non-volatile memory, or an appropriate combination thereof), one or more magnetic disk storage devices, optical disk storage devices, flash memory devices, other forms of storage media that may be accessed by the computing apparatus 12 and are configured to store desired information, or a suitable combination thereof. The communication bus 18 connects the processor 14, the computer-readable storage medium 16, and various other components of the computing apparatus 12 to one another.

Also, the computing apparatus 12 may include one or more input/output interfaces 22 for providing an interface for one or more input/output devices 24, and one or more network communication interfaces 26. The input/output interfaces 22 and the network communication interfaces 26 are connected to the communication bus 18. The input/output devices 24 may be connected to other components of the computing apparatus 12 through the input/output interfaces 22. The input/output devices 24 may include input devices such as a pointing device (a mouse, a trackpad, etc.), a keyboard, a touch input device (a touchpad, a touch screen, etc.), a voice or sound input device, various kinds of sensor devices, and/or a capture device and/or may include output devices such as a display device, a printer, a speaker, and/or a network card. The input/output devices 24 may be included in the computing apparatus 12 as components of the computing apparatus 12 and may be connected to the computing apparatus 12 as separate devices distinct from the computing apparatus 12.

Figure 2:
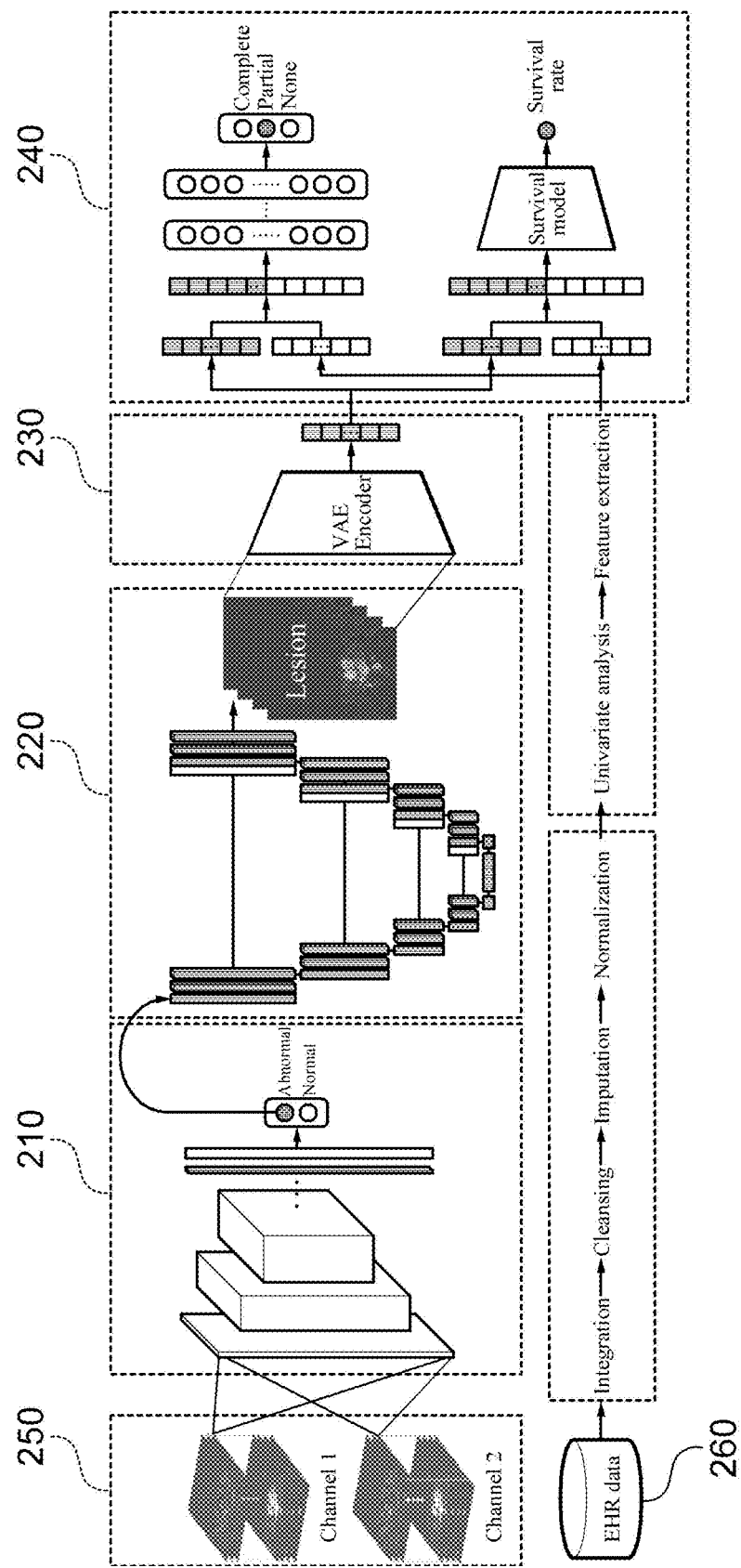
FIG. 2 is a block diagram showing a medical diagnostic system according to an embodiment.

FIG. 2 is a block diagram showing a medical diagnostic system 200 according to an embodiment.

According to an embodiment, the medical diagnostic system 200 may process each process for medical diagnosis using models trained based on deep learning and then provide a diagnosis result for an object.

Referring to FIG. 2, the medical diagnostic system 200 includes a lesion classification model 210 configured to extract at least one slide including a lesion among a plurality of slide images of a 3D medical image obtained by capturing an object, a region-of-interest (ROI) extraction model 220 configured to extract an ROI including the lesion from the slide including the lesion, and an ROI abstraction model 230 configured to generate latent space data in which a feature of an image for the ROI is compressed, and a medical diagnostic model 240 for generating a diagnosis result for the object.

In this case, the models 210, 220, 230, and 240 included in the medical diagnostic system 200 may be pre-trained, that is, may be deep learning models. The medical diagnostic system 200 may sequentially perform medical diagnostic processes using the models 210, 220, 230, and 240 in the order of the medical diagnostic processes.

The medical diagnostic system 200 may use a 3D medical image 250 obtained by capturing an object and clinical data 260 for an object as input data for medical diagnosis. The 3D medical image 250 may be captured using one or more medical image capturing apparatus. For example, the 3D medical image 250 may be captured through Magnetic Resonance Imaging (MRI), Computed Tomography (CT), etc. In this case, the 3D medical image 250 may be in the form of, for example, Digital Imaging and Communications in Medicine (DICOM), which is a standard for medical imaging. Also, when the 3D medical image 250 is captured through MRI, the 3D medical image 250 may include various sequence images such as a T1-weighted image (T1WI), a T2-weighted image (T2WI), a diffusion-weighted image (DWI), a fluid-attenuated inversion recovery (FLAIR) image, and an apparent diffusion coefficient (ADC) image.

The clinical data 260 may include object information. For example, the clinical data 260 may include the object's age, gender, height, weight, diseases, medication history, and the like. In this case, the object may be, for example, a patient with a disease.

Meanwhile, the 3D medical image 250 and the clinical data 260 may be data that is preprocessed by the computing apparatus 12 in various ways.

In an embodiment, it is assumed that a first 3D medical image and a second 3D medical image obtained by capturing the same object in different ways are used as input data for medical diagnosis in the medical diagnostic system 200.

In this case, when the 3D medical image is preprocessed, the computing apparatus 12 may perform a registration process to make the first 3D medical image and the second 3D medical image have the same modality. For example, when the sizes, origins, inter-image spacing, and the like of 2D images corresponding to the first 3D medical image are different from those of 2D images corresponding to the second 3D medical image, the computing apparatus 12 may set the second 3D medical image as a linear model and resample the second 3D medical image to correspond to the modality of the first 3D medical image. Thus, the computing apparatus 12 may make the first 3D medical image and the second 3D medical image having the same modality.

Figure 3:
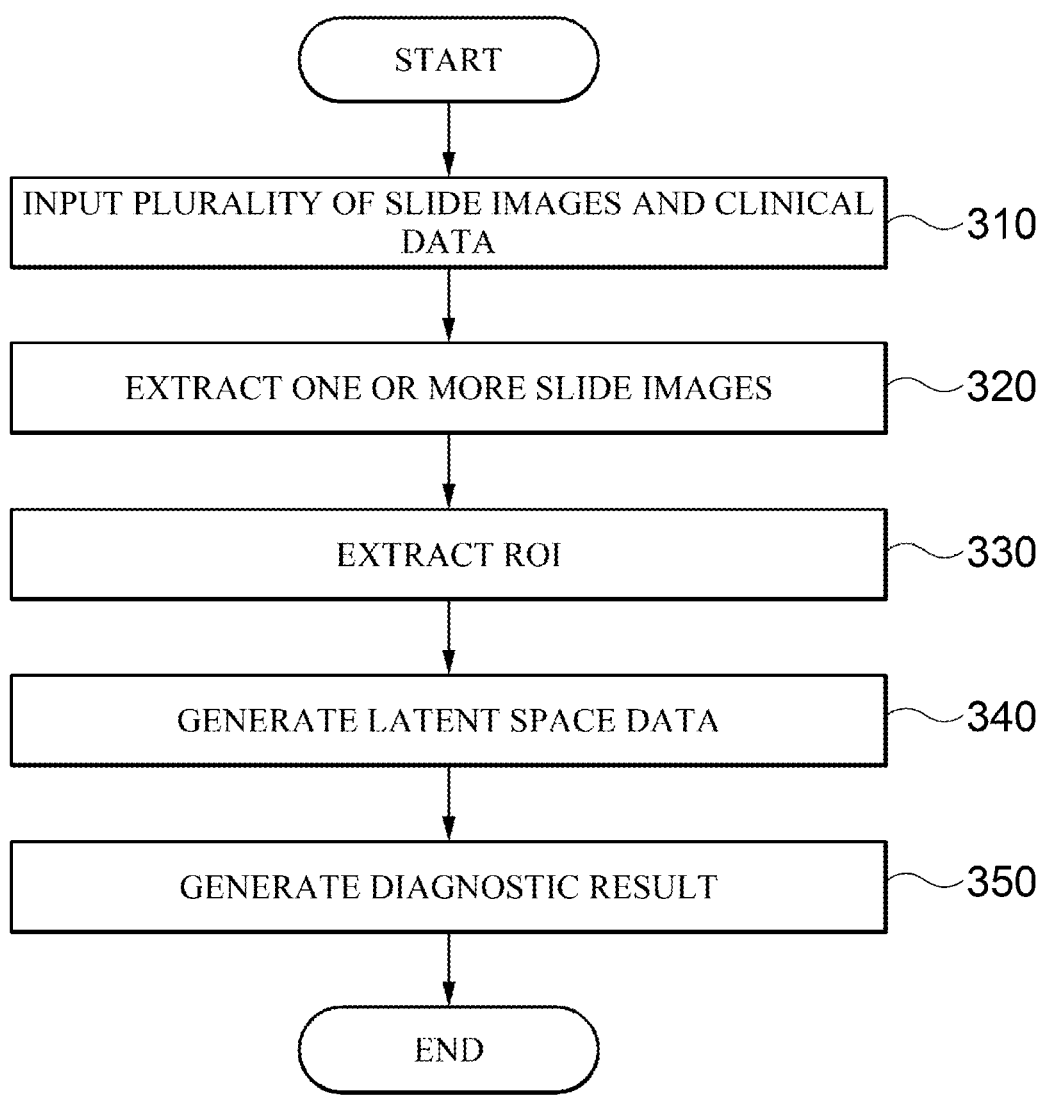
FIG. 3 is a flowchart illustrating a medical diagnostic method according to an embodiment.

Subsequently, the computing apparatus 12 may normalize the first 3D medical image and the second 3D medical image. For example, as shown in FIG. 3, the computing apparatus 12 may perform the normalization through histogram matching. In to detail, through the histogram matching, pixel values of an image may be converted according to a cumulative histogram of a reference image based on a histogram distribution of pixel values in another image.

Subsequently, the computing apparatus 12 may perform quantization into a finite number of partial segments in order to reduce the amount of computation. For example, the computing apparatus 12 may change a pixel value having a range of −30,000 to 40,000 to have a range of 0 to 255 to minimize the amount of computation of the computing apparatus 12.

After the above preprocessing process is performed, the preprocessed 3D medical image 250 may be stored in a memory provided in the computing apparatus 12 in the form of Python's NumPy library.

Meanwhile, since clinical data for objects is stored in databases of different hospitals, data stored in the databases should be integrated, and typos and incorrect inputs in clinical data should be modified. To this end, the computing apparatus 12 may preprocess the clinical data by means of imputation of missing values through the multivariate imputation by chained equations (MICE) technique using chain equations and normalization of data values with different ranges through Min-max, z-score, etc.

After the above preprocessing process is performed, the preprocessed clinical data 260 may be stored in the memory provided in the computing apparatus 12.

FIG. 3 is a flowchart illustrating a medical diagnostic method according to an embodiment.

The method illustrated in FIG. 3 may be performed by, for example, the computing apparatus 12 including a memory configured to store one or more instructions and one or more processors configured to execute the one or more instructions. In the illustrated flowchart, the method will be described to have a plurality of operations. However, at least some of the operations are performed in the exchanged order, performed in combination with another operation, are omitted, divided into sub-operations and then performed, or performed in addition to one or more operations that are not shown.

Referring to FIG. 3, the computing apparatus 12 receives a plurality of slide images of a 3D medical image obtained by capturing an object and clinical data for the object (310).

In this case, the plurality of slide images may be a plurality of 2D images into which the 3D medical image is divided.

Also, as described above, the clinical data and the plurality of slide images of the 3D medical image may be preprocessed by the computing apparatus 12.

Subsequently, the computing apparatus 12 extracts one or more slide images including a lesion among the plurality of slide images (320).

For example, by using a pre-trained convolutional neural network (CNN)-based lesion classification model 210 for classifying whether a lesion is included in a slide image, the computing apparatus 12 may extract one or more slide images including a lesion among the plurality of slide images. A process of training the lesion classification model will be described in detail below with reference to FIG. 7.

In detail, it is assumed that a plurality of preprocessed slide images of the first 3D medical image and a plurality of preprocessed slide images of the second 3D medical image are used as 2-channel input data of the lesion classification model 210. In this case, the computing apparatus 12 may determine whether a lesion exists in each slide image by inputting the plurality of slide images to the lesion classification model 210. The computing apparatus 12 may extract one or more slide images including a lesion among the plurality of slide images based on the determination result and may deliver the extracted slide images to the ROI extraction model 220.

Subsequently, the computing apparatus 12 extracts an ROI including a lesion from each of the extracted slide images (S330).

For example, by using a pre-trained CNN-based ROI extraction model 220 for extracting a region having a lesion from a slide image as an ROI, the computing apparatus 12 may extract an ROI from each of the slide images. A process of training the ROI extraction model will be described in detail below with reference to FIG. 8.

In detail, by inputting the one or more slide images including the lesion extracted using the lesion classification model 210 to the ROI extraction model 220, the computing apparatus 12 may extract an ROI including a lesion from each of the slide images. In other words, the computing apparatus 12 may input, as input data of the ROI extraction model, output data of the lesion classification model 210 that has received the plurality of slide images as input data. In this case, the computing apparatus 12 may acquire images of the ROIs extracted from each of the slide images.

Also, according to an embodiment, the computing apparatus 12 may generate a 3D ROI image obtained by combining the images of the ROIs extracted from each of the one or more slide images.

For example, the computing apparatus may generate a 3D ROI image in a 3D voxel shape by combining the images of the ROIs extracted from each of the one or more slide images. Also, the computing apparatus 12 may acquire metadata such as the sizes, origins, inter-image relationship, and the like of the 2D images of the 3D medical image from the slide images of the 3D medical image. The computing apparatus 12 may match the 3D ROI image to the 3D medical image based on location information included in the acquired metadata and store the 3D ROI image matched to the 3D medical image in the memory.

Subsequently, the computing apparatus 12 may generate latent space data including features of the images of the ROIs extracted from each of the one or more slide images using a pre-trained deep learning-based ROI abstraction model 230.

In this case, the latent space data may be data that is expressed by compressing the features of the images of the ROIs. In detail, the latent space data may be the image data about the ROIs compressed from high dimensional data to low dimensional data by the ROI abstraction model 230.

A process of training the ROI abstraction model will be described in detail below with reference to FIGS. 9 and 10.

Subsequently, the computing apparatus 12 may generate a diagnostic result for the object from the latent space data and the clinical data using a pre-trained deep learning-based medical diagnostic model 240 (350).

In this case, the diagnostic result may include one of a survival rate, a treatment status, and a lesion type classification result for the object. Accordingly, the type of the medical diagnostic model 240 may be determined based on the diagnostic type for the object.

For example, the medical diagnostic model 240 may include a survival rate prediction model for predicting the survival rate of the object. In this case, the survival rate prediction model may be a deep learning model using a partial likelihood-based loss function of the Cox proportional hazards model.

Also, the medical diagnostic model 240 may include a classifier model for classifying the treatment status of the object as complete response, partial response, and no response. In this case, according to an embodiment, the classifier model may classify the type of the lesion as well as the above-described treatment status. For example, when diagnosing breast cancer of an object, the classification model may classify the type of the breast cancer as Type A, Type B, Type H, Type T, and the like.

The above example illustrates that the diagnostic result includes one of a survival rate, a treatment status, and a lesion type classification result. However, the present invention is not limited thereto, and the diagnostic result may include various medical diagnoses for an object. Thus, the medical diagnostic model 240 may also include various models.

Meanwhile, a process of training the medical diagnostic model will be described in detail below with reference to FIGS. 9 and 10.

Figure 4:
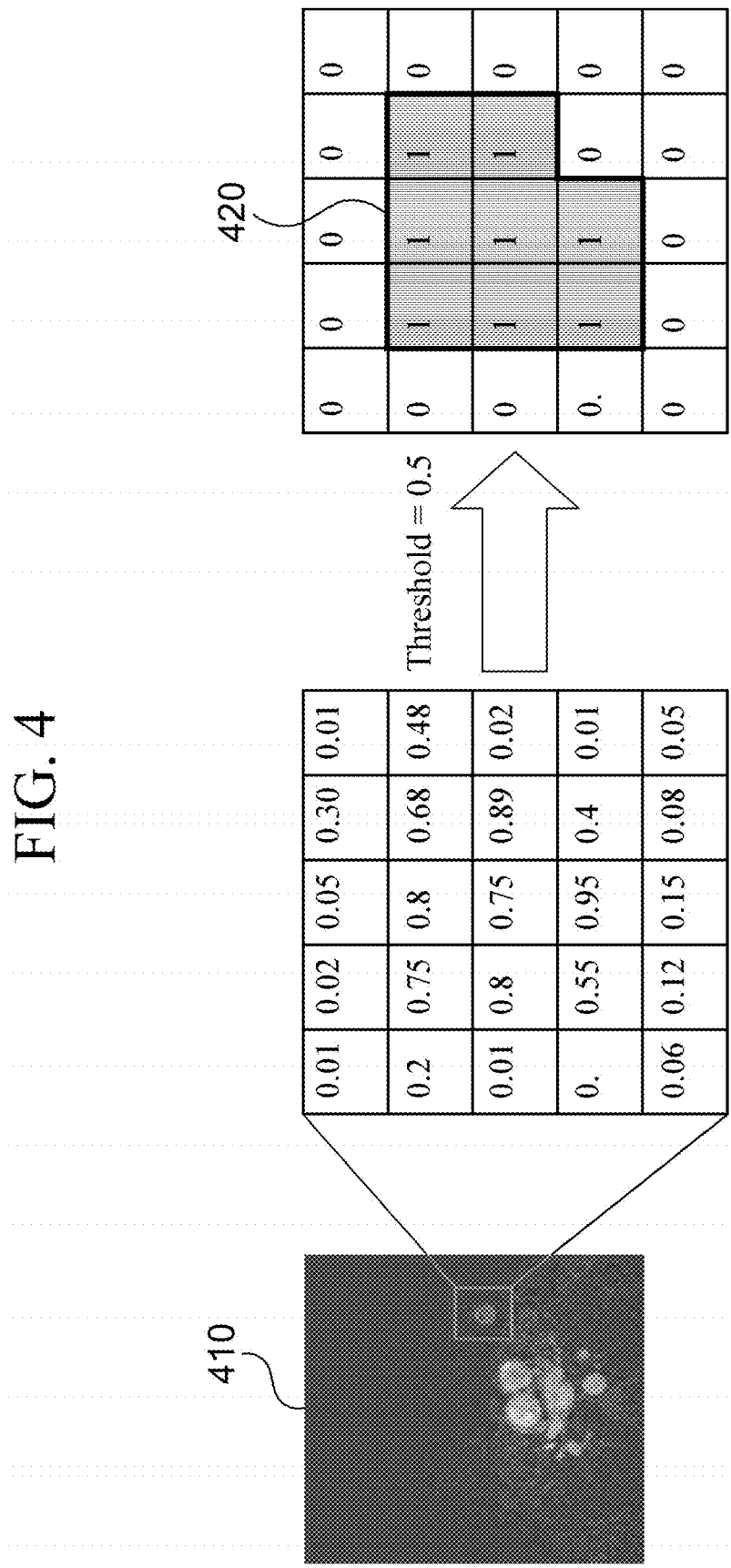
FIG. 4 is a diagram illustrating an example of extracting a region of interest (ROI) according to an embodiment.

FIG. 4 is a diagram illustrating an example of extracting an ROI according to an embodiment.

Referring to FIG. 4, the computing apparatus 12 may extract an ROI from one or more slide images using the ROI extraction model 220. For example, the ROI extraction model 220 may calculate a probability that each pixel of a slide image 410 will correspond to an ROI including a lesion. Subsequently, the ROI extraction model 220 may extract pixels having probabilities greater than or equal to a preset threshold among a plurality of pixels included in the slide image and may extract a region including the extracted pixels as an ROI 420.

Figure 5:
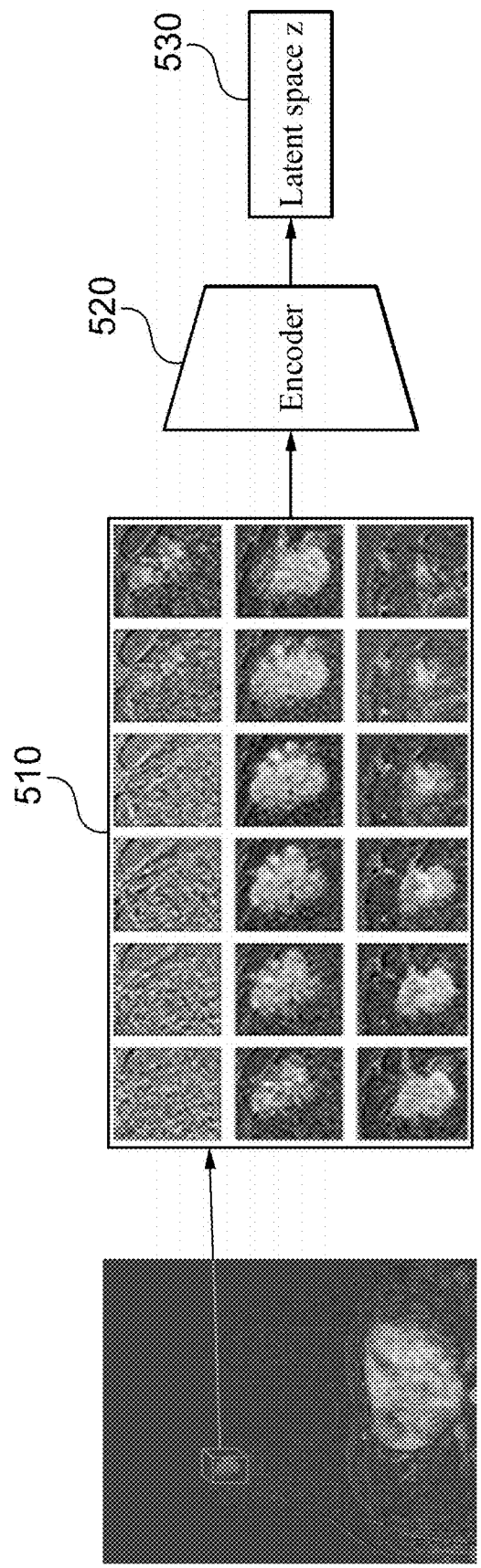
FIG. 5 is a diagram illustrating an example of generating latent space data according to an embodiment.

FIG. 5 is a diagram illustrating an example of generating latent space data according to an embodiment.

Referring to FIG. 5, the computing apparatus 12 may generate latent space data including a feature of an image of an ROI using the ROI abstraction model 230. In an embodiment, the ROI abstraction model 230 may include an encoder 520 that is trained using images of a plurality of ROIs including a lesion as training data through variational auto-encoder (VAE). Accordingly, the computing apparatus 12 may generate latent space data 530 by encoding image data 510 about ROIs extracted from one or more slide images using an encoder 520 trained through VAE.

For example, when there are 18 images of an ROI including a pixel having a size of 48*48, the image data 510 about the ROI extracted from each of the one or more slide images may have 47472 dimensions. In this case, the encoder 520 may encode high-dimensional image data 510 to generate latent space data 530 having 20 dimensions.

FIG. 6 is an exemplary diagram of a diagnostic result according to an embodiment.

(a) of FIG. 6 shows a graph for a baseline of a cumulative hazard function, (b) of FIG. 6 shows a survival prediction graph for Object A, (c) of FIG. 6 shows a graph for a baseline of a survival function, and (d) of FIG. 6 shows a survival prediction graph for Object B. Also, in each graph, the y-axis represents a fraction and the x-axis represents a survival period. The unit of the survival period represented by the x axis of the graph shown in FIG. 6 has been described as "month" but may be set to be "day" or "year" depending on the embodiment.

Referring to FIG. 6, it is assumed that the medical diagnostic model 240 is a survival rate prediction model for predicting the survival rate of an object. The medical diagnostic model 240 may predict a change in the object such as death, disease recurrence, and the like with the passing of time. The medical diagnostic model 240 may generate a survival prediction function for an object from the latent space data and clinical data for the object. Subsequently, the medical diagnostic model 240 may calculate a period-specific survival probability for the object based on the survival prediction function.

In detail, there is a 75% probability that Object A is predicted to survive for 150 to 200 months, and also there is a 75% probability that Object B is predicted to survive to for 50 to 100 months. Accordingly, a user may determine that Object A will survive longer than Object B using the medical diagnostic model 240.

Figure 7:
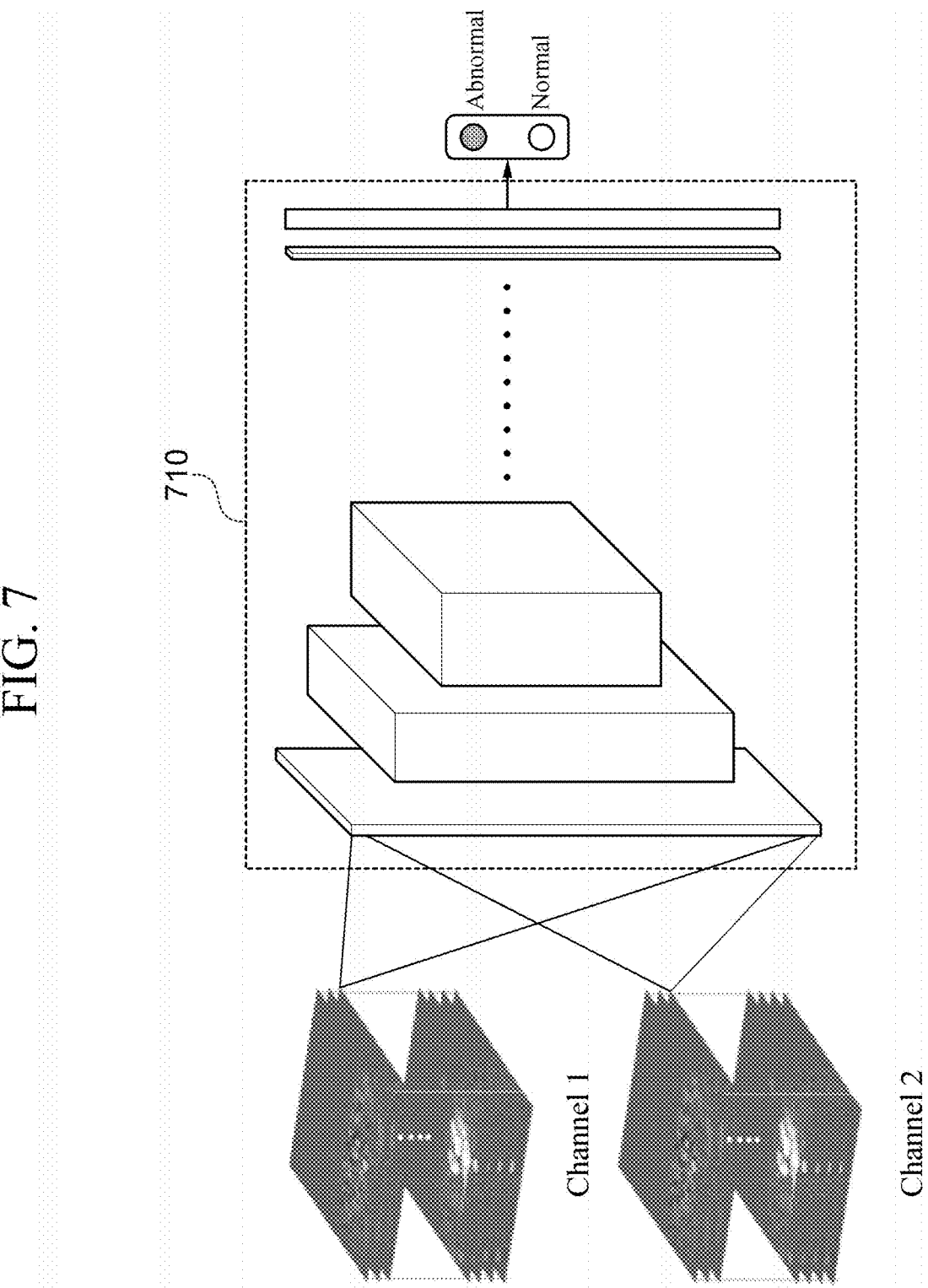
FIG. 7 is a diagram illustrating an example of training a lesion classification model according to an embodiment.

FIG. 7 is a diagram illustrating an example of training a lesion classification model according to an embodiment.

Referring to FIG. 7, the computing apparatus 12 may train a lesion classification model 710 using a plurality of pre-collected slide images and a lesion classification result for each of the plurality of pre-collected slide images as training data. The lesion classification model 710 may be, for example, a CNN-based deep learning model. In an embodiment, for example, the lesion classification model 710 may have a similar structure to the image classification model such as ResNet.

In this case, the lesion classification result may be target data allocated to a plurality of pre-collected slide images by a user (annotation). In this case, the user may include one or more radiology specialists. For example, the user may allocate a lesion classification result to each of the plurality of slide images using a 3D modeling program such as ITK-SNAP.

In detail, the computing apparatus 12 may train the lesion classification model 710 using the plurality of pre-collected slide images as input data and also using the lesion classification results for the plurality of pre-collected slide images as target data.

In this case, a loss function for the lesion classification model 710 may include at least one of a variety of known loss functions such as, for example, a binary cross-entropy loss function, a multi-class support vector machine loss function, and the like.

Also, whether the lesion classification model 710 is well trained may be evaluated through an evaluation indicator such as specificity, sensitivity, and F1 score indicating a harmonic mean value of precision and recall. Accordingly, the computing apparatus 12 may select the highest-rated lesion classification model among a plurality of trained lesion classification models as a model to be used in the medical diagnostic system 200.

Figure 8:
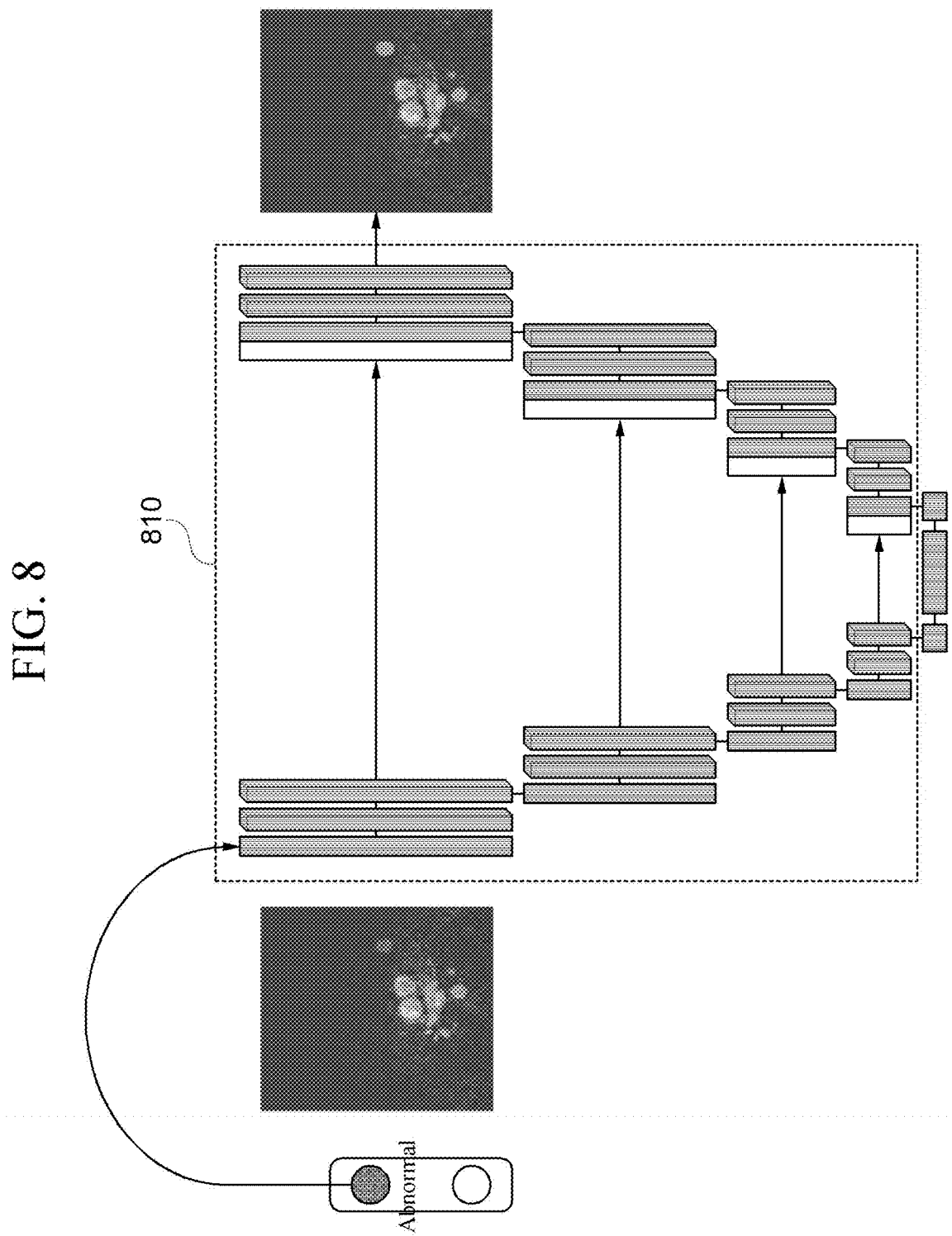
FIG. 8 is a diagram illustrating an example of training an ROI extraction model according to an embodiment.

FIG. 8 is a diagram illustrating an example of training an ROI extraction model according to an embodiment.

Referring to FIG. 8, the computing apparatus 12 may train an ROI extraction model 810 using a plurality of pre-collected slide images including a lesion and an ROI extraction result for each of the plurality of pre-collected slide images as training data.

The ROI extraction model 810 may be, for example, a CNN-based deep learning model. In an embodiment, the ROI extraction model 810 may have a similar structure to an image segmentation model such as U-Net, the Mask Region-based Convolutional Neural Network (mask-RCNN), and you only look once (YOLO).

Meanwhile, the ROI extraction result may be target data allocated by a user in the same way as that of the lesion classification result.

In detail, the computing apparatus 12 may train the ROI extraction model 810 using a plurality of pre-collected slide images including a lesion as input data and also using an ROI extraction result for each of the plurality of pre-collected slide images as target data.

In this case, a loss function for the ROI extraction model 810 may include at least one of a variety of known loss functions such as, for example, the binary cross-entropy loss function, the focal loss function, the dice loss function, and the like.

Also, whether the ROI extraction model 810 is well trained may be evaluated through an evaluation indicator such as, for example, a 3D intersection over union (IoU). Accordingly, the computing apparatus 12 may select the highest-ranked ROI extraction model among a plurality of trained ROI extraction models as a model to be used in the medical diagnostic system 200.

Figure 9:
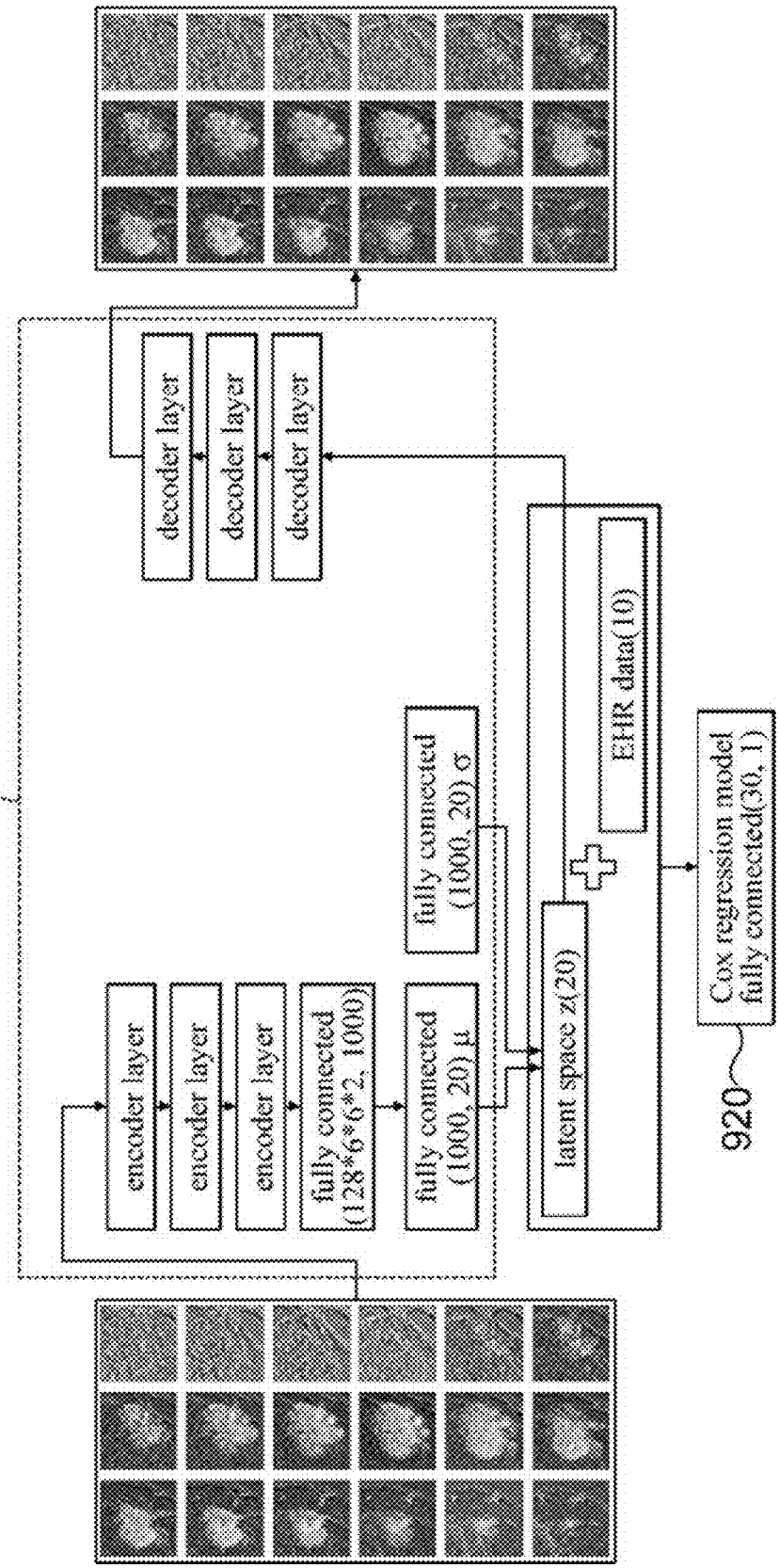
FIGS. 9 and 10 are diagrams illustrating examples of training ROI abstraction models and medical diagnostic models according to an embodiment.
Figure 10:
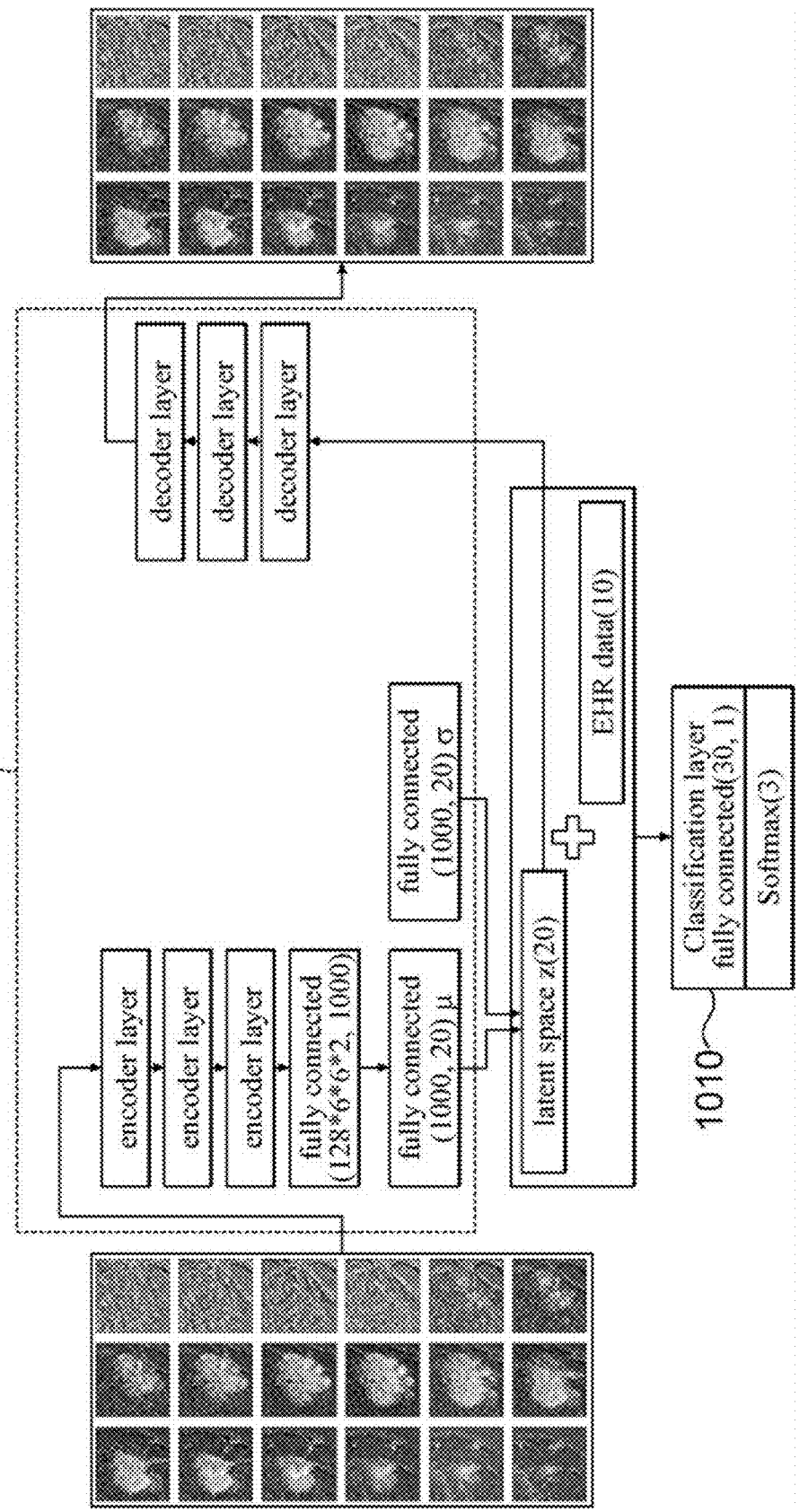

FIGS. 9 and 10 are diagrams illustrating examples of training ROI abstraction models and medical diagnostic models according to an embodiment.

The medical diagnostic models shown in FIGS. 9 and 10 illustrate a survival rate prediction model 920 for predicting the survival rate of an object and a classifier model 1010 for predicting the treatment status of an object. In detail, FIG. 9 illustrates that the medical diagnostic model is the survival rate prediction model 920, and FIG. 10 illustrates that the medical diagnostic model is the classifier model 1010. Also, as described above, the medical diagnostic models shown in FIGS. 9 and 10 are illustrated as the survival rate prediction model 920 and the classifier model 1010. However, this is merely an example, and the medical diagnostic models may include various models depending on the type of medical diagnosis for an object.

Referring to FIGS. 9 and 10, the computing apparatus 12 may train both of an ROI abstraction model and a medical diagnostic model.

An ROI abstraction model 910 may receive images of a plurality of ROIs including a lesion as training data. As described above, the ROI abstraction model 910 may be trained through VAE. For example, the ROI abstraction model 910 may include an encoder, a hidden layer, and a decoder.

In the disclosed embodiments, the encoder and decoder included in the ROI abstraction model 910 are not limited to specific structures and may have various structures configured depending on the settings.

Also, the hidden layer included in the medical diagnosis model may be connected to the ROI abstraction model 910 and may be trained along with the ROI abstraction model 910. In this case, the hidden layer included in the medical diagnostic model may include, for example, a fully-connected layer. Also, when the medical diagnostic model is the classifier model 1010, a softmax function-based classifier may be included.

The computing apparatus 12 may train the medical diagnostic model using a plurality of pieces of clinical data, a diagnostic result for each of the plurality of pieces of clinical data, and output data of the ROI abstraction model 910 which has received the images of the plurality of ROIs including the lesion as training data.

TABLE 1

| Patient | Age | Radiotherapy | Survival Period (Months) | Still Surviving |
|---|---|---|---|---|
| 1 | 28 | ○ | 8 | X |
| 2 | 44 | X | 15 | ○ |
| 3 | 32 | ○ | 22 | X |
| 4 | 16 | X | 24 | X |
| ... | ... | ... | ... | ... |

TABLE 2

| Patient | Age | Radiotherapy | Chemotherapy | Treatment Status |
|---|---|---|---|---|
| 1 | 28 | ○ | Cisplatin | Complete Response (CR) |
| 2 | 44 | X | Herceptin | Partial Response (PR) |
| 3 | 32 | ○ | Perjeta | No Response (NR) |
| 4 | 16 | X | Cisplatin | Complete Response (CR) |
| ... | ... | ... | ... | ... |

Table 1 and Table 2 illustrate a plurality of pieces of clinical data and a diagnostic result for each of the plurality of pieces of clinical data. Table 1 represents data used for the survival rate prediction model 920, and Table 2 represents data used for the classifier model 1010.

For example, the plurality of pieces of clinical data may include the age, radiotherapy, chemotherapy, and the like of a plurality of patients, and the diagnostic result for each of the plurality of pieces of clinical data may include the survival or death, the survival period, and the treatment status of each of a plurality of patients. In this case, the diagnostic result may be pre-acquired from a hospital or the like before the medical diagnostic model is trained.

In detail, the computing apparatus 12 may train the medical diagnostic model using a plurality of pieces of clinical data and latent space data generated by the encoder of the ROI abstraction model 910 which has received the images of the plurality of ROIs as input data and also using the diagnostic result for each of the plurality of pieces of clinical data as target data. That is, a compressed feature of the images of the plurality of ROIs may be extracted through the hidden layer of the ROI abstraction model 910 while the ROI abstraction model 910 is trained. In this case, the compressed feature indicates the latent space data, and may be an original data from which a redundant feature included in the original data of the images of the plurality of ROIs may be removed.

Thus, the medical diagnostic model uses a compressed feature from which a redundant feature of an image of an ROI is removed as training data and also uses clinical data and latent space data compressed with low-dimensional data as training data, and thus it is possible to increase the accuracy of the diagnostic result of the medical diagnostic model.

Meanwhile, the ROI abstraction model 910 and the medical diagnostic model may be trained such that a sum of a resulting value of a loss function of each of the ROI abstraction model 910 and the medical diagnostic model is minimized as expressed in Equation 1 below.

In this case, the sum of the resulting value of the loss function of each of the ROI abstraction model 910 and the medical diagnostic model may be calculated through Equation 1 below:

$$L_{total} = \alpha \cdot \text{VAE\_loss} + \text{Diagnostic\_loss} \text{ (here, } 0 < \alpha) \quad \text{[Equation 1]}$$

where $L_{total}$ indicates the sum of the resulting value of the loss function of each of the ROI abstraction model 910 and the medical diagnostic model, VAE_loss indicates a resulting value of a loss function of the ROI abstraction model 910, and Diagnostic_loss indicates a resulting value of a loss function of the medical diagnostic model.

In detail, the sum of the resulting value of the loss function of each of the ROI abstraction model 910 and the medical diagnostic model may be represented as the sum of the resulting value of the loss function of the medical diagnostic model and the resulting value of the loss function of the ROI abstraction model 910 to which a variable a is assigned as a weight.

Meanwhile, the loss function of the medical diagnostic model may differ depending on the type of the medical diagnostic model. For example, when the medical diagnostic model is the survival rate prediction model 920, the loss function of the medical diagnostic model may be a partial likelihood-based loss function of the Cox proportional hazards model. On the other hand, when the medical diagnostic model is the classifier model 1010, the loss function of the medical diagnostic model may be a cross-entropy-based loss function.

Accordingly, by the ROI abstraction model 910 and the medical diagnostic model being trained such that the sum of the resulting value of the loss function of each of the ROI abstraction model 910 and the medical diagnostic model is minimized, a user may acquire the ROI abstraction model 910 optimized for the medical diagnostic model through the above training scheme. Thus, the medical diagnostic model uses output data of the ROI abstraction model 910 optimized for the corresponding medical diagnostic model as input data during the medical diagnosis process, and thus it is possible to increase the accuracy of the diagnostic result for the medical diagnostic model.

In this case, the resulting value of the loss function of the ROI abstraction model 910 may be calculated using Equation 2 below:

$$\text{VAE\_loss} = \text{BCE} + \beta \text{KLD} \text{ (here, } 0 \leq \beta \leq 1) \quad \text{[Equation 2]}$$

where BCE indicates a binary cross-entropy-based loss function, and indicates a Kullback-Leibler divergence-based loss function.

In detail, the computing apparatus 12 may set the value of a variable β to zero and thus train the ROI abstraction model 910 primarily using only the binary cross-entropy-based loss function. Subsequently, the computing apparatus 12 may train the ROI abstraction model 910 while gradually increasing the value of the variable 13 to gradually increase the ratio of the Kullback-Leibler divergence-based loss function to the loss function of the ROI abstraction model 910.

Accordingly, the training is performed in consideration of a plurality of pieces of latent variable data including a feature of an image of an ROI as a whole, and thus it is possible to solve a problem of certain latent variable data not being properly trained by the Kullback-Leibler divergence-based loss function.

Meanwhile, whether the ROI extraction model 910 is well trained may be evaluated through the amount of decrease of the loss function of the ROI extraction model 910. Whether the survival rate prediction model included in the medical diagnostic model is well trained may be evaluated through an evaluation indicator such as a concordance index. Whether the classifier model included in the medical diagnostic model is well trained may be evaluated through an evaluation indicator such as specificity, sensitivity, and F1 score indicating a harmonic mean value of precision and recall. Accordingly, the computing apparatus 12 may select the highest-ranked ROI abstraction model and medical diagnostic model among a plurality of trained ROI abstraction models and medical diagnostic models as a model to be used in the medical diagnostic system 200.

In the examples shown in FIGS. 9 and 10, the number marked in each image or each hidden layer is for representing the dimension of data and is merely an example. Therefore, the present invention is not necessarily limited thereto.

The technical features have been described with reference to the embodiments. However, the disclosed embodiments should be considered in a descriptive sense only and not for purposes of limitation. Therefore, the scope of the invention is defined not by the detailed description of the invention but by the appended claims, and all differences within the scope will be construed as being included in the present invention.

The invention claimed is:
1. A medical diagnostic method comprising:
receiving a plurality of slide images of a three-dimensional (3D) medical image obtained by capturing an object and clinical data in addition to the plurality of slide images for the object;
extracting one or more slide images including a lesion among the plurality of slide images;
extracting a region of interest (ROI) including the lesion from each of the extracted one or more slide images;
generating latent space data including a feature of an image of the extracted ROI using a pre-trained deep learning-based ROI abstraction model comprising an encoder that is trained using images of a plurality of ROIs including a lesion as training data; and
generating a diagnostic result for the object from the latent space data and the clinical data using a pre-trained deep learning-based medical diagnostic model, wherein the medical diagnostic model is trained using a plurality of pieces of clinical data, a diagnostic result for each of pieces of the clinical data, and output data of the ROI abstraction model as training data.

2. The medical diagnostic method of claim 1, wherein the extracting of one or more slide images comprises extracting the one or more slide images using a convolutional neural network (CNN)-based lesion classification model that is pre-trained using a plurality of pre-collected slide images and a lesion classification result for each of the plurality of pre-collected slide images as training data.

3. The medical diagnostic method of claim 1, wherein the extracting of an ROI comprises extracting the ROI using a CNN-based ROI extraction model that is pre-trained using a plurality of pre-collected slide images including a lesion and an ROI extraction result for each of the plurality of pre-collected slide images as training data.

4. The medical diagnostic method of claim 1, wherein the encoder is trained using the images of the plurality of ROIs including the lesion as the training data through variational auto-encoder (VAE).

5. The medical diagnostic method of claim 4, wherein the generating of latent space data comprises generating the latent space data by using the encoder to encode the image of the extracted ROI.

6. The medical diagnostic method of claim 1, wherein the ROI abstraction model and the medical diagnostic model are trained such that a sum of a resulting value of a loss function of each of the ROI abstraction model and the medical diagnostic model is minimized.

7. The medical diagnostic method of claim 6, wherein the sum of the resulting value of the loss function of each of the ROI abstraction model and the medical diagnostic model is calculated using Equation 1 below:

$$L_{total} = \alpha \cdot \text{VAE\_loss} + \text{Diagnostic\_loss} \text{ (here, } 0 < \alpha\text{)} \quad \text{[Equation 1]}$$

where $L_{total}$ indicates the sum of the resulting value of the loss function of each of the ROI abstraction model and the medical diagnostic model, VAE_loss indicates a resulting value of a loss function of the ROI abstraction model, and Diagnostic_loss indicates a resulting value of a loss function of the medical diagnostic model.

8. The medical diagnostic method of claim 1, wherein the diagnostic result comprises one of a survival rate, a treatment status, and a lesion type classification result.

9. The medical diagnostic method of claim 1, further comprising, after the extracting of an ROI, generating a 3D ROI image obtained by combining the image of the extracted ROI of each of the extracted one or more slide images.

10. A medical diagnostic apparatus comprising:
a memory configured to store one or more instructions; and
one or more processors configured to execute the one or more instructions,
wherein the one or more processors:
receive a plurality of slide images of a three-dimensional (3D) medical image obtained by capturing an object and clinical data in addition to the plurality of slide images for the object,
extract one or more slide images including a lesion among the plurality of slide images,
extract a region of interest (ROI) including the lesion from each of the extracted one or more slide images,
generate latent space data in which a feature of an image of the extracted ROI is compressed using a pre-trained deep learning-based ROI abstraction model comprising an encoder that is trained using images of a plurality of ROIs including the lesion as training data, and
generate a diagnostic result for the object from the latent space data and the clinical data using a pre-trained deep learning-based medical diagnostic model,
wherein the medical diagnostic model is trained using a plurality of pieces of clinical data, a diagnostic result for each of pieces of the clinical data, and output data of the ROI abstraction model as training data.

11. The medical diagnostic apparatus of claim 10, wherein the one or more processors extract the one or more slide images using a convolutional neural network (CNN)-based lesion classification model that is pre-trained using a plurality of pre-collected slide images and a lesion classification result for each of the plurality of pre-collected slide images as training data.

12. The medical diagnostic apparatus of claim 10, wherein the one or more processors extract the ROI using a CNN-based ROI extraction model that is pre-trained using a plurality of pre-collected slide images including a lesion and an ROI extraction result for each of the plurality of pre-collected slide images as training data.

13. The medical diagnostic apparatus of claim 10, wherein the encoder is trained using the images of the plurality of ROIs including the lesion as the training data through variational auto-encoder (VAE).

14. The medical diagnostic apparatus of claim 13, wherein the one or more processors generate the latent space data by using the encoder to encode the image of the extracted ROI.

15. The medical diagnostic apparatus of claim 10, wherein the ROI abstraction model and the medical diagnostic model are trained such that a sum of a resulting value of a loss function of each of the ROI abstraction model and the medical diagnostic model is minimized.

16. The medical diagnostic apparatus of claim 15, wherein the sum of the resulting value of the loss function of each of the ROI abstraction model and the medical diagnostic model is calculated using Equation 1 below:

$$L_{total} = \alpha \cdot \text{VAE\_loss} + \text{Diagnostic\_loss} \text{ (here, } 0 < \alpha\text{)} \quad \text{[Equation 1]}$$

where $L_{total}$ indicates the sum of the resulting value of the loss function of each of the ROI abstraction model and the medical diagnostic model, VAE_loss indicates a resulting value of a loss function of the ROI abstraction model, and Diagnostic_loss indicates a resulting value of a loss function of the medical diagnostic model.

17. The medical diagnostic apparatus of claim 10, wherein the diagnostic result comprises one of a survival rate, a treatment status, and a lesion type classification result.

18. The medical diagnostic apparatus of claim 10, wherein the one or more processors generate a 3D ROI image obtained by combining the image of the extracted ROI of each of the extracted one or more slide images.

* * * * *